US009226720B2

United States Patent
Tanaka et al.

(10) Patent No.: US 9,226,720 B2
(45) Date of Patent: Jan. 5, 2016

(54) RADIOGRAPHIC APPARATUS

(71) Applicant: SHIMADZU CORPORATION, Kyoto-shi, Kyoto (JP)

(72) Inventors: Masahiro Tanaka, Kyoto (JP); Takanori Yoshida, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 278 days.

(21) Appl. No.: 13/679,949

(22) Filed: Nov. 16, 2012

(65) Prior Publication Data

US 2014/0140476 A1    May 22, 2014

(51) Int. Cl.
| G01N 23/04 | (2006.01) |
| A61B 6/04 | (2006.01) |
| A61B 6/06 | (2006.01) |
| A61B 6/00 | (2006.01) |

(52) U.S. Cl.
CPC ............... *A61B 6/0457* (2013.01); *A61B 6/06* (2013.01); *A61B 6/405* (2013.01); *A61B 6/469* (2013.01); *A61B 6/545* (2013.01); *A61B 6/586* (2013.01); *A61B 6/0442* (2013.01); *A61B 6/4085* (2013.01); *A61B 6/4435* (2013.01); *A61B 6/461* (2013.01); *A61B 6/542* (2013.01); *A61B 6/582* (2013.01)

(58) Field of Classification Search
USPC .............. 378/1, 34, 35, 50, 62, 145, 147, 150
See application file for complete search history.

(56) References Cited

U.S. PATENT DOCUMENTS

| 5,170,425 A | 12/1992 | Haendle | |
| 2008/0247509 A1 | 10/2008 | Kashiwagi | |
| 2009/0220046 A1* | 9/2009 | Ji et al. ............................ | 378/65 |
| 2010/0054408 A1* | 3/2010 | Echner ............................ | 378/65 |
| 2011/0150179 A1* | 6/2011 | Kato ............................... | 378/62 |

FOREIGN PATENT DOCUMENTS

| JP | 62-195800 U | 12/1987 |
| JP | 2-041143 A | 2/1990 |
| JP | 5-103263 A | 4/1993 |

(Continued)

OTHER PUBLICATIONS

Japanese Office Action issued in Japanese Application No. 2010-099943 issued Nov. 12, 2013.

*Primary Examiner* — Nicole Ippolito
*Assistant Examiner* — Hanway Chang
(74) *Attorney, Agent, or Firm* — McDermott Will & Emery LLP (57) ABSTRACT

A radiographic apparatus comprising, a radiation source for emitting radiation, a radiation detecting device having a detecting surface for detecting radiation, an image generating device for generating images in accordance with detection data outputted from the radiation detecting device, a collimator for restricting spread of a radiation beam emitted from the radiation source, an opening-degree obtaining device for obtaining a degree of opening of the collimator and a display device for displaying a radiation-irradiation area on the image, the opening-degree obtaining device determining the radiation-irradiation area to be displayed on the image in accordance with a relationship between a width of the radiation beam contained in the image obtained in advance by two or more degrees of opening of the collimator through radiation irradiation and the degrees of opening of the collimator as well as the current degree of opening of the collimator.

6 Claims, 6 Drawing Sheets

(56) References Cited

FOREIGN PATENT DOCUMENTS

| | | | |
|---|---|---|---|
| JP | 2008-253555 A | 10/2008 | |
| JP | 2009-183373 A | 8/2009 | |
| JP | 2009-291472 A | 12/2009 | |

* cited by examiner

| DEGREE OF OPENING | WIDTH | DEVIATION AMOUNT | TOP-BOARD INCLINATION | X-RAY TUBE INCLINATION |
|---|---|---|---|---|
| 100% | 1,024 | 0 | 0 | 0 |
| 90% | 940 | −40 | 0 | 0 |
| 10% | 75 | 0 | 0 | 0 |
| 0% | 0 | 15 | 0 | 0 |

Prior art

RADIOGRAPHIC APPARATUS

TECHNICAL FIELD

This invention relates to a radiographic apparatus for taking images through irradiating a subject with radiation. More particularly, this invention is directed to a radiographic apparatus having a collimator that can open and close freely to change spread of a radiation beam.

BACKGROUND

Figure 11:
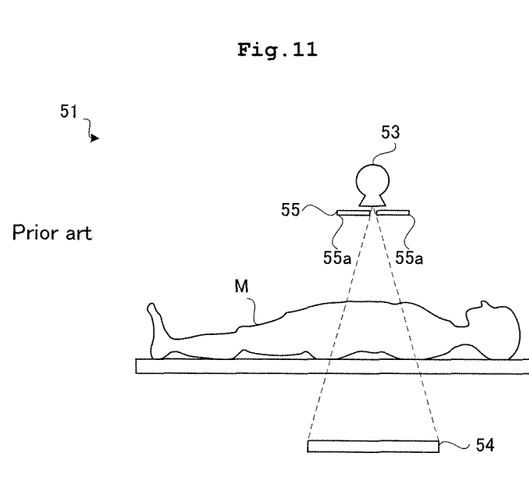
FIG. 11 is a schematic view illustrating a conventional X-ray apparatus.

Medical institutions have a radiographic apparatus installed therein for taking images of a subject. As shown in FIG. 11, such a radiographic apparatus 51 includes a radiation source 53 for emitting radiation, and a radiation detector 54 for detecting the radiation.

The radiation source 53 includes a collimator 55 that can open and close freely to change spread of a radiation beam. The collimator 55 has a pair of leaves 55a. They approach and move away, thereby restricting a direction of radiation emitted from the radiation source 53.

When an operator instructs opening and closing of the collimator 55 via a console, the radiographic apparatus 51 calculates a movement extent of the leaves 55a. For instance, when a slider set on the console is operated, the radiographic apparatus 51 recognizes how many centimeters the leaves 55a are to be moved in accordance with a distance by which a lever of the slider moves, and moves the leaves 55a by the calculated distance relative to a drive controller for the leaves 55a of the collimator 55. See, Japanese Utility Model (Registration) Publication No. S62-195800.

The leaves are schematically displayed on a monitor attached to the radiographic apparatus 51. The leaves displayed on the monitor as a graphic symbol are moved in accordance with a degree of opening of the actual leaves 55a. Recognition of the leaves on the monitor by an operator can cause confirmation a of a restricted extent of a radiation beam. A position of the leaves 55a on this monitor is determined in accordance with the calculated degree of opening indicating how many centimeters the leaves 55a are moved.

When the operator gives instructions on radiation irradiation via the console, the radiation source 53 emits radiation. Here, the collimator 55a restricts the radiation beam. The restricted extent is same as that confirmed by the operator prior to radiation irradiation. As above, the leaves on the monitor are moved synchronously with the actual leaves 55a, whereby spread of the radiation beam upon radiation irradiation can be determined in advance.

The conventional construction, however, has the following problem.

The conventional radiographic apparatus 51 has a problem that the degree of opening of the collimator indicated by the leaves 55a displayed on the monitor differs from the degree of opening of the actual collimator 55. Such problem arises. Under this state, although the operator confirms the leaves 55a on the monitor, the operator cannot recognize accurately the restricted extent of an actual irradiation direction of the radiation beam.

Description will be given of how such inconsistencies in degree of opening of the collimator occur. For changing the degree of opening of the collimator 55, it is firstly determined how many centimeters the leaves 55a are to be moved corresponding to a distance by which a lever of a slider on a console moves. Subsequently, a drive controller for the leaves 55a of the collimator 55 moves the leaves 55a by the distance as determined. However, the leaves 55a are not always moved correctly by the distance as set.

There are two or more reasons for an inaccurate movement distance of the leaves 55a. Firstly, a mechanism for moving the leaves 55a causes an inaccurate movement distance of the leaves 55a. The leaves 55a are moved as a rotatable arm rotates. Consequently, the leaves 55a are not moved horizontally but are moved along an arc path close to a straight line. When the leaves 55a are moved by a given distance, the arm rotates by a given angle, accordingly. Thus, when the arm is moved by the same angle, a length of the path by which the leaves 55a follow through the movement is always the same. However, since the path is not a straight line, the collimator 55 does not always have the degree of opening as set. As noted above, the leaves 55a are moved along the arc path. Thus, although the arm is moved by the same angle, difference in initial position of the leaves 55a causes slight difference in movement distance of the leaves 55a.

Moreover, it is difficult to position and attach the collimator 55 onto the radiation source 53 accurately. A slight deviation in position of the collimator 55 and the radiation source 53 from an ideal position will affect actual radiography sufficiently. Specifically, a slight deviation of the collimator 55 is enlarged as the radiation beam emitted from the radiation source 53 spreads toward a subject M. Consequently, although a deviation in fixing position of the collimator 55 and the radiation source 53 is around 0.1 mm, a position of the radiation beam emitted to the subject M may be order of magnitude of centimeters. In addition, a deviation in position of the radiation source 53 and the radiation detector 54 from an ideal position causes a deviation in relative position of the leaves 55a of the collimator 55 relative to both the components 53, 54. Accordingly, an ideal position of the leaves 55a on the monitor deviates from the actual position of the leaves 55a.

Since the leaves 55a of the collimator 55 displayed on the monitor are moved in accordance with output from the drive controller for the leaves 55a, a position of the leaves 55a specified by the drive controller is displayed on the monitor. The actual leaves 55a of the collimator 55 are not always moved as the ideal. Consequently, inconsistencies in degree of opening occur between the actual collimator 55 and the collimator 55 on the monitor. Therefore, it is difficult for an operator to recognize an accurate irradiation area of the radiation beam prior to radiation irradiation.

SUMMARY

This invention has been made regarding the state of the art noted above, and its object is to provide a radiographic apparatus having a collimator, the apparatus being able to recognize spread of a radiation beam prior to radiation irradiation through indicating a degree of opening of the collimator accurately on a monitor.

This invention is constituted as stated below to achieve the above object.

That is, a radiographic apparatus of this invention include a radiation source for emitting radiation; a radiation detecting device having a detecting surface for detecting radiation; an image generating device for generating images in accordance with detection data outputted from the radiation detecting device; a collimator for restricting spread of a radiation beam emitted from the radiation source; an opening-degree obtaining device for obtaining a degree of opening of the collimator; and a display device for displaying a radiation-irradiation area on the image. The opening-degree obtaining device determining the radiation-irradiation area on the image to be displayed in accordance with a current degree of opening of the collimator and a relationship between a width of the radiation beam and the degrees of opening of the collimator, the width of the radiation beam being contained in the image obtained in advance by two or more degrees of opening of the collimator.

According to this example of the invention, provided is the display device for displaying the radiation-irradiation area on the image. It is difficult to actually control the collimator according to the degree of opening of the collimator specified by an operator. In other words, when the operator opens and closes the collimator, inconsistencies occur in the degree of opening of the actual collimator and the collimator displayed on the display device. That is because leaves of the collimator are not always moved as an ideal when opening and closing conditions of the collimator are displayed on the display device. As a result, this example includes the opening-degree obtaining device that determines the radiation-irradiation area on the image to be displayed in accordance with a current degree of opening of the collimator and a relationship between a width of a radiation beam and the degree of opening of the collimator, the width of the radiation beam being contained in the image obtained in advance by two or more degreed of opening of the collimator through radiation irradiation. The radiation-irradiation area stored in the opening-degree obtaining device has an actual measurement value that is obtained in accordance with the width of the radiation beam contained in the image obtained through radiation irradiation. The display device displays a radiation-irradiation area for the radiation detecting device in accordance with the radiation-irradiation area. Thereby, the operator can recognize an accurate irradiation area of the radiation beam with reference to the display device prior to radiation irradiation. Moreover, this can achieve saved time and effort for fluoroscopy, and in addition a reduced inspection time when many inspections are to be conducted.

Moreover, in the aforementioned radiographic apparatus, the relationship between the width of the radiation beam and the degree of opening of the collimator is a correlated table representing a relationship between the width of the radiation beam contained in the image obtained through radiation irradiation and the degree of opening of the collimator. Such configuration is more desirable.

The aforementioned configuration shows a specific relationship between the width of the radiation beam and the degree of opening of the collimator. When the relationship between the width of the radiation beam and the degree of opening of the collimator is a correlated table having a relationship between the width of the radiation beam and the degree of opening of the collimator, the opening-degree obtaining device can readily obtain the radiation-irradiation area by merely referring to the correlated table.

It is more desirable that the aforementioned radiographic apparatus further includes a correlated-table interpolating device for interpolating the correlated table to generate a new correlated table having an increased number of components than that in the correlated table.

The aforementioned configuration shows a specific relationship between the width of the radiation beam and the degree of opening of the collimator to which the opening-degree obtaining device refers. The correlated table is obtained through conducting radiography two or more times while the degree of opening of the collimator changes. That is, the correlated table is generated while the degree of opening of the collimator gradually changes. Consequently, the correlated table with higher accuracy can be obtained by taking images for more degrees of opening of the collimator with small variation in opening of the collimator. On the other hand, this leads to increased frequency of taking images, resulting in complex generation of the correlated table. Thus interpolating calculation for increasing the number of components in the correlated table can obtain a reliable correlated table without increasing the number of measurement.

Moreover, in the aforementioned radiographic apparatus, the relationship between the width of the radiation beam and the degree of opening of the collimator is a relational expression having a relationship between the width of the radiation beam contained in the image obtained through radiation irradiation and the degree of opening of the collimator. Such configuration is more desirable.

The aforementioned configuration shows a specific relationship between the width of the radiation beam and the degree of opening of the collimator to which the opening-degree obtaining device refers. The relational expression having a relationship between the width of the radiation beam and the degree of opening of the collimator can obtain the same effect as that in the correlated table with a smaller amount of information than the correlated table. Thereby, the radiographic apparatus has increased flexibility for the elements.

Moreover, the aforementioned radiographic apparatus further includes a radiation-source inclining device for inclining the radiation source relative to the radiation detecting device; and a radiation-source inclination controlling device for controlling the radiation-source inclining device. The relationship between the width of the radiation beam and the degree of opening of the collimator is obtained through conducting radiography two or more times while the radiation source is inclined relative to the radiation detecting device. Such configuration is more desirable.

The foregoing configuration can achieve a radiation-irradiation area with higher accuracy that is displayed on the display device. A positional relationship of the radiation source, the collimator, and the radiation detecting device deviates as the radiation source is inclined relative to the radiation detecting device. Accordingly, the position of the radiation beam in the radiation detecting device changes as the radiation source is inclined. Where the relationship between the width of the radiation beam and the degree of opening of the collimator generated with inclination of the radiation source conforming to radiography conditions is used upon obtaining the radiation-irradiation area by the opening-degree obtaining device, the radiation-irradiation area is displayed on the display device taking into consideration the influences due to inclination of the radiation source. Consequently, the operator can recognize an accurate position of radiation irradiation via the display device independently of the inclination of the radiation source. Moreover, this can achieve a reduced exposure dose to the subject.

The foregoing radiographic apparatus further includes a top board for supporting the subject placed thereon between the radiation source and the radiation detecting device; a top-board inclining device for inclining the top board with a positional relationship between the radiation source and the radiation detecting device being maintained; and a top-board inclination controller for controlling the top-board inclining device. The relationship between the width of the radiation beam and the degree of opening of the collimator is obtained through conducting radiography two or more times while the top board is inclined. Such a configuration is more desirable.

The foregoing configuration can achieve a radiation-irradiation area with higher accuracy that is displayed on the display device. Since the radiation source is heavy, the radiation source is directed downward as the top board is inclined. Accordingly, the position of the radiation beam on the detecting surface of the radiation detecting device changes as the top board is inclined. The relationship between the width of the radiation beam and the degree of opening of the collimator generated with the inclination of the top board conforming to radiography conditions is used upon obtaining the radiation-irradiation area by the opening-degree obtaining device. Thereby the radiation-irradiation area is displayed on the display device taking into consideration influences due to inclination of the top board. Consequently, the operator can recognize an accurate position of radiation irradiation via the display device independently of the inclination of the top board. Moreover, this can achieve a reduced exposure dose to the subject.

DETAILED DESCRIPTION

One example of this invention will be described hereinafter. X-rays in examples correspond to the radiation in this invention. An FPD is the abbreviation of a flat panel detector.

Figure 1:
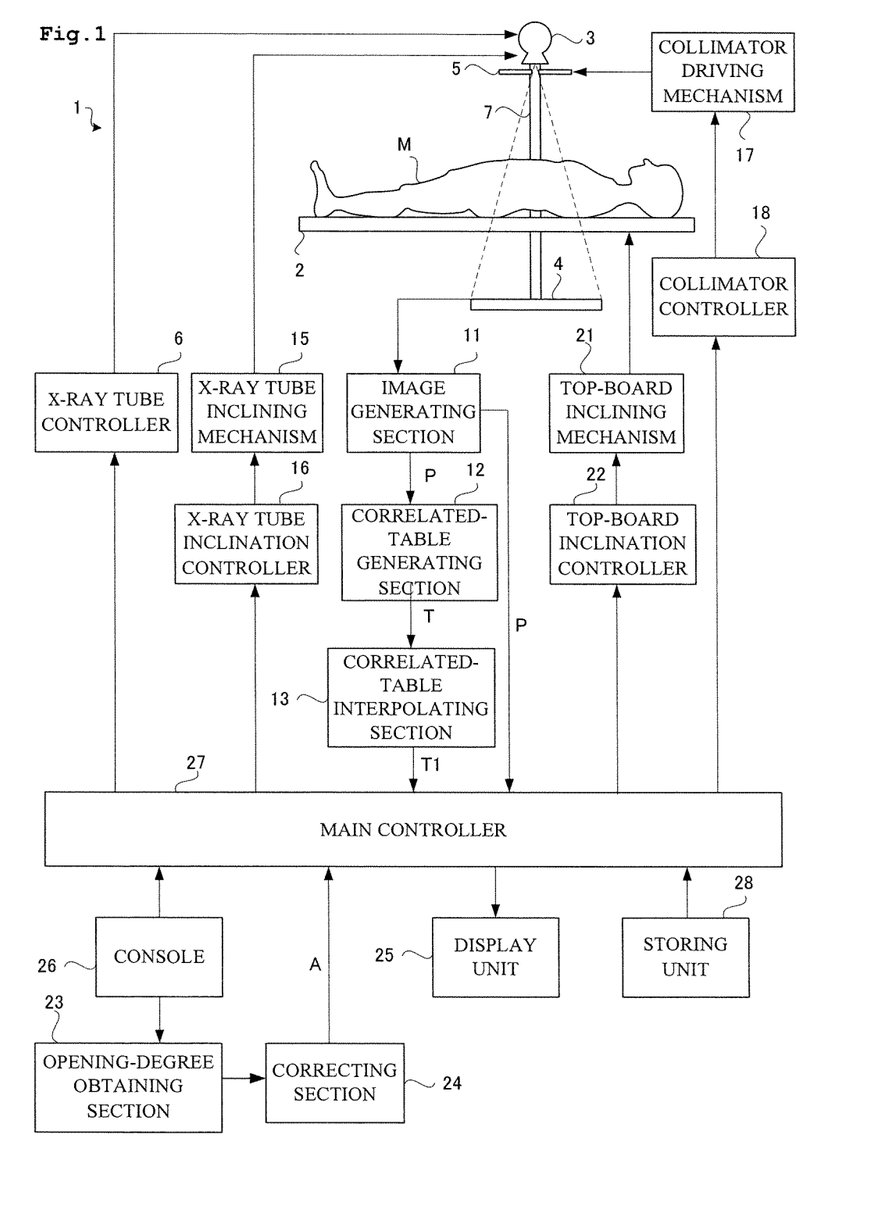
FIG. 1 is a functional block diagram illustrating an X-ray apparatus according to one example.

Firstly, description will be given of an X-ray apparatus 1 according to Example 1. As shown in FIG. 1, the X-ray apparatus 1 includes a top board 2 for supporting a subject M placed thereon, an X-ray tube 3 above the top board 2 for emitting X-rays, and an FPD 4 below the top board 2 for detecting X-rays. The FPD 4 has a detecting surface for detecting X-rays. The X-ray tube 3 has a collimator 5 attached thereto whose degree of opening can be controlled freely. Controlling the degree of opening of the collimator 5 can control spread of a radiation beam emitted from the X-ray tube 3. The X-ray tube 3 corresponds to the radiation source in this invention. The FPD 4 corresponds to the radiation detecting device in this invention.

An X-ray tube controller 6 is provided for controlling the X-ray tube 3 with a given tube current, a tube voltage, and a pulse width. The FPD 4 detects X-rays emitted from the X-ray tube 3 and transmitting through the subject M, and generates a detection signal. The detection signal is sent out to an image generating section 11, where an image P is generated having a projected image of the subject M containing therein. The image generating section 11 corresponds to the image generating device in this invention.

A correlated-table generating section 12 is provided for generating a correlated table T, to be mentioned later, from the image P. Moreover, a correlated-table interpolating section 13 is further provided for interpolating the correlated table T to increase the number of components that forms the table. Here, detail of each section 12, 13 will be described later. The correlated-table interpolating section 13 corresponds to the correlated-table interpolating device in this invention.

Figure 2:
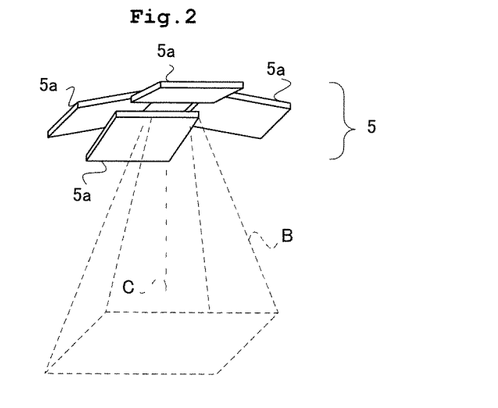
FIG. 2 is a perspective view illustrating a collimator according to the example.

Description will be given in detail of the collimator 5. As shown in FIG. 2, the collimator 5 has one pair of leaves 5a that moves in a mirror-image symmetrical manner relative to a center axis C, and has one more pair of leaves 5a that similarly moves in a mirror-image symmetrical manner relative to the center axis C. Movement of the leaves 5a of the collimator 5 can achieve not only irradiation of an entire detection surface of the FPD 4 with an X-ray beam B in a cone shape, but also irradiation of only a center portion of the FPD 4 with an X-ray beam B in a fan shape. Here, the center axis C also represents the center of the X-ray beam B. One pair of the leaves 5a controls spread of the quadrangular pyramid X-ray beam in a long-side direction of the top board. The other pair of the leaves 5a controls spread of the X-ray beam in a short-side direction of the top board. A collimator driving mechanism 17 changes the degree of opening of the collimator 5. A collimator controller 18 controls the collimator driving mechanism 17. The collimator controller 18 corresponds to the collimator control device in this invention.

The leaves 5a of the collimator 5 are supported by a rotatable arm, not shown. The leaves 5a are moved through rotation of the arm, whereby the degree of opening of the collimator 5 is changed. Consequently, the leaves 5a are moved along an arc path upon changing the degree of opening of the collimator 5. The arm is attached to the collimator driving mechanism 17.

Figure 3:
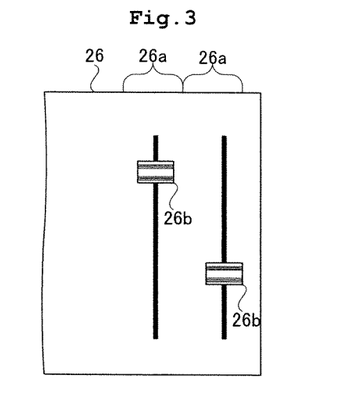
FIG. 3 is a plan view illustrating a console according to the example.

A console 26 is provided for inputting operator's instructions. Specifically, examples of the operator's instructions include setting parameters, such as a tube voltage and a tube current, with respect to control of the X-ray tube 3, and radiation irradiation. As shown in FIG. 3, the console 26 includes a slide rheostat 26a. The slide rheostat 26a has an upper side indicating a larger degree of opening of the collimator 5 and a lower side indicating a smaller degree of opening of the collimator 5. The console 26 corresponds to the opening-variation input device in this invention.

An opening-degree obtaining section 23 obtains a direction of movement and a target opening of the leaves 5a of the collimator 5 in accordance with input of the slide rheostat 26a. When the operator moves a lever 26b of the slide rheostat 26a upward by a manipulated variable, the opening-degree obtaining section 23 calculates movement of the leaves 5a proportional to the manipulated variable and the degree of opening of the collimator 5 specified by the operator, and then recognizes that a pair of leaves 5a has to be moved by the calculated degree of opening of the collimator such that they are spaced away. When the operator moves the lever 26b downward, the opening-degree obtaining section 23 recognizes that the pair of leaves 5a has to be moved such that they approach.

The degree of opening of the collimator outputted from the opening-degree obtaining section 23 is sent to a correcting section 24. The correcting section 24 outputs a correction value A corresponding to the degree of opening of the collimator outputted from the opening-degree obtaining section 23 with reference to a correlated table T. The correlated table T has a correlation between the degree of opening of the collimator outputted from the opening-degree obtaining section 23 and the width of the X-ray beam (a correction value A)

contained in the image P outputted from the image generating section 11. The correcting section 24 corresponds to the correcting device in this invention.

Figure 4:
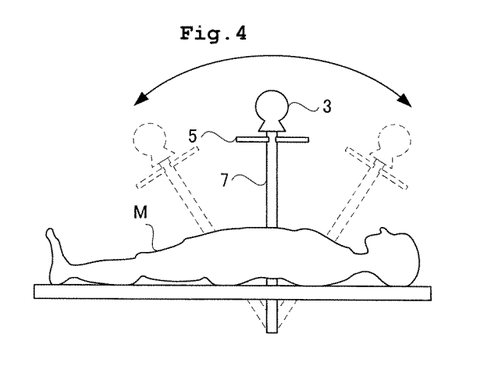
FIG. 4 is a schematic view illustrating inclination of an X-ray tube according to the example.

The X-ray tube 3 is supported by a strut 7. An X-ray tube inclining mechanism 15 is provided for inclining the X-ray tube 3 relative to the top board 2. By the X-ray tube inclining mechanism 15, the X-ray tube 3 can be inclined so as to approach one end of the top board 2 in a long-side direction and so as to be moved away. This is controlled by an X-ray tube inclination controller 16. In actual, as shown in FIG. 4, the X-ray tube inclination mechanism 15 inclines the strut 7 relative to the top board 2, thereby inclining the X-ray tube 3. Here, the collimator 5 is inclined together with the X-ray tube 3 with the positional relationship between the collimator 5 and the X-ray tube 3 being maintained. The X-ray tube inclination controller 16 corresponds to the radiation-source inclination control device in this invention. The X-ray tube inclining mechanism 15 corresponds to the radiation-source inclining device in this invention.

Figure 5:
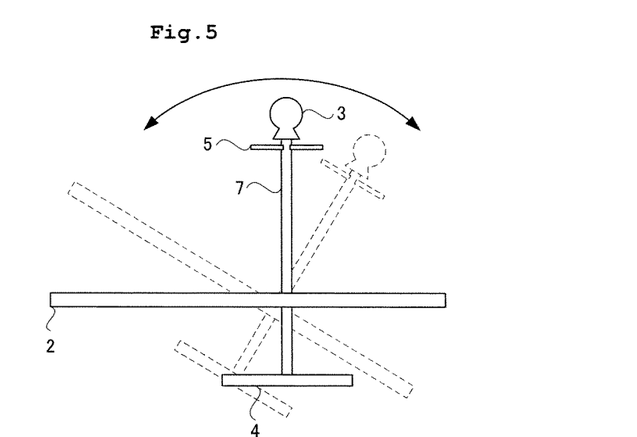
FIG. 5 is a schematic view illustrating inclination of a top board according to the example.

A top-board inclining mechanism 21 is provided for inclining the top board 2 through rotating the top board 2 about the center axis in a short-side direction of the top board 2 (i.e., a body axis direction of the subject.) The top board 2 can be inclined by the top-board inclining mechanism 21 such that one end of the top board 2 in the long-side direction can be directed downward and upward. Accordingly, the X-ray tube 3, the FPD 4, the collimator 5, and the strut 7 are inclined integrally while the positional relationship thereof between the top board 2 is maintained. A top-board inclination controller 22 is provided for controlling the top-board inclining mechanism 21.

A display unit 25 is provided for displaying the image P of the subject. Moreover, a main controller 27 is provided for performing an overall control of each controller. The main controller 27 has a CPU, and provides each controller 6, 11, 12, 13, 16, 18, 22, 23, 24 by executing various programs. The above components may be divided into arithmetic units that perform their functions. A storing unit 28 stores all of parameters, such as the correlated table T, with respect to control of the X-ray apparatus 1. The display unit 25 corresponds to the display device in this invention.

<Generation of Correlated Table>

Next, description will be given of a method of generating a correlated table to which the correcting section 24 refers. The correlated table T is generated in advance by a correlated-table generating section 12 prior to taking an image of the subject placed on the top board 2.

For generating the correlated table T, radiography is firstly conducted setting a degree of opening of the collimator 5 to be 100% while the subject is not placed on the top board 2. The image P taken under this state is sent out to the correlated-table generating section 12, where a length of the leaves 51 contained in the image P is measured. Where a shadow of the leaves 5a is not contained in the image P at this time, the correlated-table generating section 12 correlates with the degree of opening of the collimator of 100% a value indicating an overall width of the FPD 4.

Subsequently, radiography is repeatedly conducted while the degree of opening of the collimator 5 gradually decreases, and the obtained image P is successively sent out to the correlated-table generating section 12. The correlated-table generating section 12 determines the length of the leaves 5a contained in each image P, and calculates the width of the X-ray beam contained in the image P. That is, radiography is conducted two or more times while the degree of opening of the collimator 5 is changed.

Figure 6:
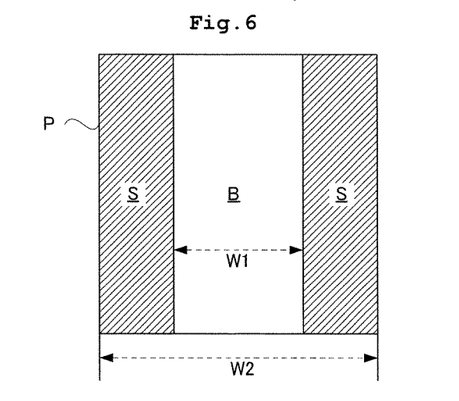
FIG. 6 is a plan view illustrating a method of obtaining a correlated table according to the example.

FIG. 6 shows an image P taken with the degree of opening of the collimator 5 of 50%. The image P contains on both ends thereof a shadow S of the leaves extending vertically. The image P has a center area where the X-ray beam is contained (an X-ray beam area B) and where the shadow S of the leaves 5a is not contained. The correlated-table generating section 12 determines a width W1 of the X-ray beam area B that varies in accordance with opening and closing of the collimator 5, and correlates the value with the degree of opening of the collimator of 50%. Since the collimator 5 has a degree of opening of 50%, the width W1 of the beam area B should be half an overall width W2 of the image P. However, as noted above, the width W1 is not always half the width W2 precisely due to movement of the leaves 5a along the arc path. That is because the collimator controller 18 is controlled on the assumption that the leaves 5a move linearly. Moreover, a deviation in positional relationship of each member 3, 4, and 5 also results in inconsistencies between the width W1 and the half of the width W2.

Figure 7:
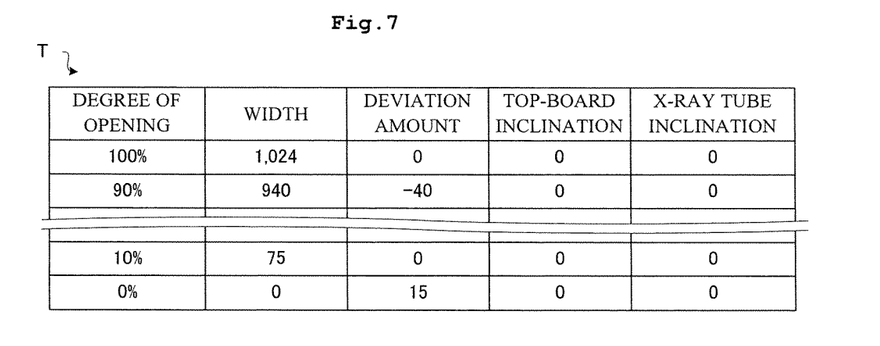
FIG. 7 is a schematic view illustrating the correlated table according to the example.

The correlated-table generating section 12 continues correlation of the degree of opening of the collimator with the width W1 of the beam area B until the degree of opening of the collimator falls into 0%, thereby generating a correlated table T as shown in FIG. 7. A deviation in amount in FIG. 7 shows to which side of the two shadows S the X-ray beam area B appears for every opening of the collimator. The X-ray beam area B exist between the two shadows S. The deviation in amount corresponds to a deviation in width between the center of the X-ray beam B and the center of the image P. FIG. 7 includes top-board inclination that shows inclination of the top board 2 for every angle upon taking the image P. Likewise, FIG. 7 includes X-ray tube inclination that shows inclination of the X-ray tube 3 for every angle upon taking the image P.

The correlated table T is sent out to the correlated-table interpolating section 13. The correlated-table interpolating section 13 determines the width W1 of the beam area B by interpolation calculation for the degree of opening of the collimator that is not in the correlated table T, and then correlates the degree of opening of the collimator with the value of the calculated width to add it into the correlated table T. The original correlated table T is obtained by each 10% reduction in degree of opening of the collimator (see FIG. 7). Consequently, the correlated-table interpolating section 13 performs the foregoing operations for the degree of opening of the collimator, for example, of 95% and 85%. The table generated in this way is called a correlated table T1. The correlated table T1 is a new table having an increased number of components than that of the correlated table T.

The correlated table T1 is stored in the storing unit 28. Here, the foregoing operations of the correlated-table interpolating section 13 may be omitted, and the correlated table T1 outputted from the correlated-table generating section 12 may be stored in the storing unit 28.

<Operation of X-ray Apparatus>

Figure 8:
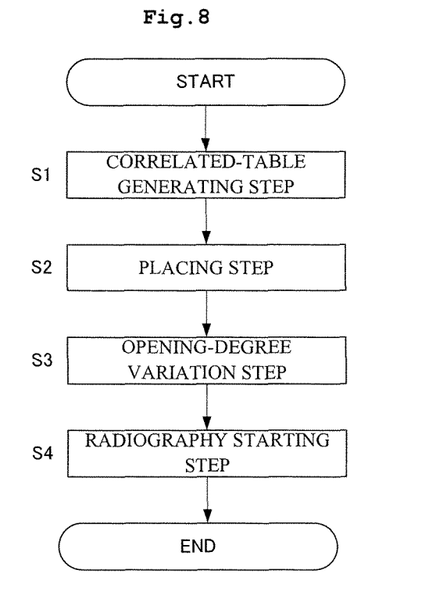
FIG. 8 is a flow chart illustrating operations of the X-ray apparatus according to the example.

Next, description will be given of operations of the X-ray apparatus 1. As shown in FIG. 8, for imaging a subject using an X-ray apparatus 1 according to Example 1, a correlated table T is firstly generated with the subject not being placed on the top board 2 (a correlated-table generating step S1), and then the subject M is placed on the top board 2 (a placing step S2.) Thereafter, a degree of opening of the collimator 5 is controlled by an operator (an opening-degree variation step S3) to start radiography (a radiography starting step S4.) Each of these steps will be described in order.

<Correlated-Table Generating Step S1>

Radiography is conducted while the subject is not placed on the top board 2. Thereby an image P is generated changing the degree of opening of the collimator 5, and the obtained image P is sent out to the correlated-table generating section 12. The correlated-table generating section 12 generates a correlated table T in accordance with a plurality of obtained images P. Here, the correlated table T has a correlation between the degree of opening of the collimator 5 and the width W1 of the X-ray beam contained in the image P. The collimator 5 has two pairs of leaves 5a, i.e., one pair of leaves 5a that moves along a long-side direction of the top board and one pair of leaves 5a that moves along a short-side direction of the top board. Consequently, two correlated tables T are to be generated individually for each of the two pairs of leaves 5a having different movement directions.

<Placing Step S2>

The operator places the subject on the top board 2, and specifies parameters with respect to control of the X-ray tube 3 or radiographic forms for the X-ray apparatus 1 via the console 26.

<Opening-Degree Variation Step S3>

When the operator operates the lever 26b of the slide rheostat 26a on the console 26, the opening-degree obtaining section 23 obtains a degree of opening of the collimator 5 specified through operation of the operator. The degree of opening of the collimator has a desired value for the degree of opening of the collimator 5 as the operator's operation. The degree of opening obtained by the opening-degree obtaining section 23 is sent out to the collimator controller 18, where the collimator 5 is controlled in accordance with the degree of opening of the collimator. On the other hand, when the operator moves the leaves 5a according to the degree of opening of the collimator, inconsistencies occur in degree of opening of the actual collimator 5 and that obtained by the opening-degree obtaining section 23 due to a mechanistic problem of the collimator driving mechanism 17 and a problem on a fixing position of the collimator 5. Consequently, when positional information of the collimator 5 outputted from the opening-degree obtaining section 23 is displayed on the display unit 25, the displayed opening of the collimator 5 is inconsistent with the actual degree of opening of the collimator 5.

Thus in this example, the degree of opening of the collimator obtained by the opening-degree obtaining section 23 is corrected so as to display the degree of opening of the collimator 5 accurately on the display unit 25. Specifically, the opening-degree obtaining section 23 sends out the obtained degree of opening of the collimator to the correcting section 24. The correcting section 24 obtains a value of a width of the X-ray beam area (specifically, a value on a right row in FIG. 7: referred to as a correction value A) corresponding to the degree of opening of the collimator in accordance with the correlated table T stored in the storing unit 28 and the sent degree of opening of the collimator.

Figure 9:
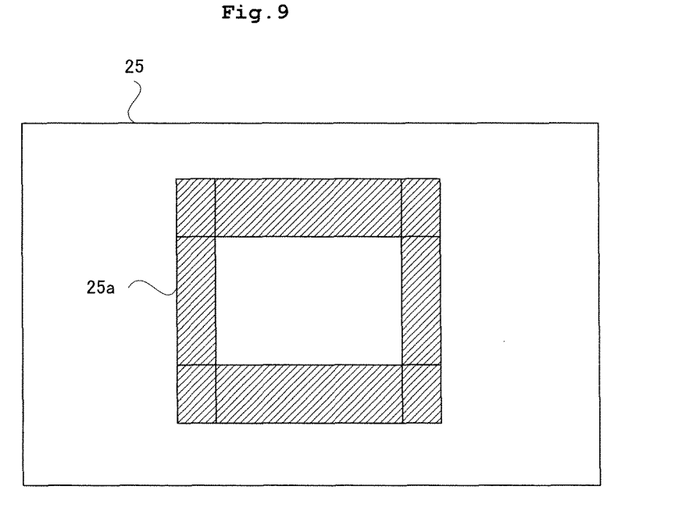
FIG. 9 is a schematic view illustrating operations of the X-ray apparatus according to the example.

On the other hand, the correction value A is sent out to the display unit 25. As shown in FIG. 9, the display unit 25 displays a rectangle 25a that imitates the FPD 4, and displays a frame shape around the rectangle 25a that imitates the leaves 5a of the collimator 5. The display unit 25 changes a size of the frame shape in accordance with the correction value A sent out from the correcting section 24. Since the correction value A is updated every time an operator controls the degree of opening of the collimator 5, the operator can observe in real time an irradiation area of the X-ray beam (X-ray irradiation area) on the FPD 4 through the display unit 25. Moreover, the display unit 25 performs display as above using the corrected position of the leaves 5a sent out from the correcting section 24. Consequently, it is taken into consideration that the leaves 5a are not moved according to the degree of opening outputted from the opening-degree obtaining section 23. Thereby, inconsistencies can be avoided in position of the collimator 5 displayed on the display unit 25 and the collimator 5 contained in the image to be taken in the next radiography starting step S4. Moreover, the display unit 25 may display the frame shape shifted from the rectangle 25a with reference to a deviation amount that forms the correlated table T.

<Radiography Starting Step S4>

The degree of opening of the collimator 5 is controlled, and thereafter X-rays are emitted from the X-ray tube 3 upon giving an instruction of starting X-ray irradiation to the X-ray apparatus 1 via the console 26 by the operator. X-rays are restricted in its emitting direction by the collimator 5, and then transmit through the subject to be detected by the FPD 4. Then detection signals from the FPD 4 are outputted to an image generating section 11, and the generated image is displayed on the display unit 25. Thus an inspection is completed.

According to Example 1, the opening-degree obtaining section 23 is provided for obtaining the degree of opening of the collimator 5 specified by the operator. It is difficult to control the collimator 5 actually according to the degree of opening of the collimator 5 specified by the operator. In other words, when the operator opens and closes the collimator 5, inconsistencies occur in degree of opening of the actual collimator 5 and the collimator 5 displayed on the display unit 25. That is because the leaves 5a of the collimator 5 are not always moved as an ideal when opening and closing conditions of the collimator are displayed on the display unit 25. Then, Example 1 includes the correcting section 24 for correcting the degree of opening of the collimator. The correction data to which the correcting section 24 refers is an actual measurement value that is obtained in accordance with the width of the X-ray beam contained in the image P obtained through X-ray irradiation. The display unit 25 displays the X-ray irradiation area on the FPD 4 in accordance with output from the correcting section 24. Consequently, the operator can recognize an accurate irradiation area of X-ray beam prior to X-ray irradiation through referring to the display unit 25.

The aforementioned configuration shows a specific configuration of the correction data to which the correcting section 24 refers. The correlated table T is obtained through conducting radiography two or more times while the degree of opening of the collimator 5 changes. That is, the correlated table T is generated through radiography while the degree of opening of the collimator 5 changes gradually. Consequently, the correlated table T with higher accuracy can be obtained by taking images P for more degree of opening of the collimator with small variation in degree of opening of the collimator 5. On the other hand, this leads to increased frequency of taking images P, resulting in complex generation of the correlated table T. Thus interpolating calculation for increasing the number of components in the correlated table T can obtain a reliable correlated table T without increasing the number of measurement.

Figure 10:
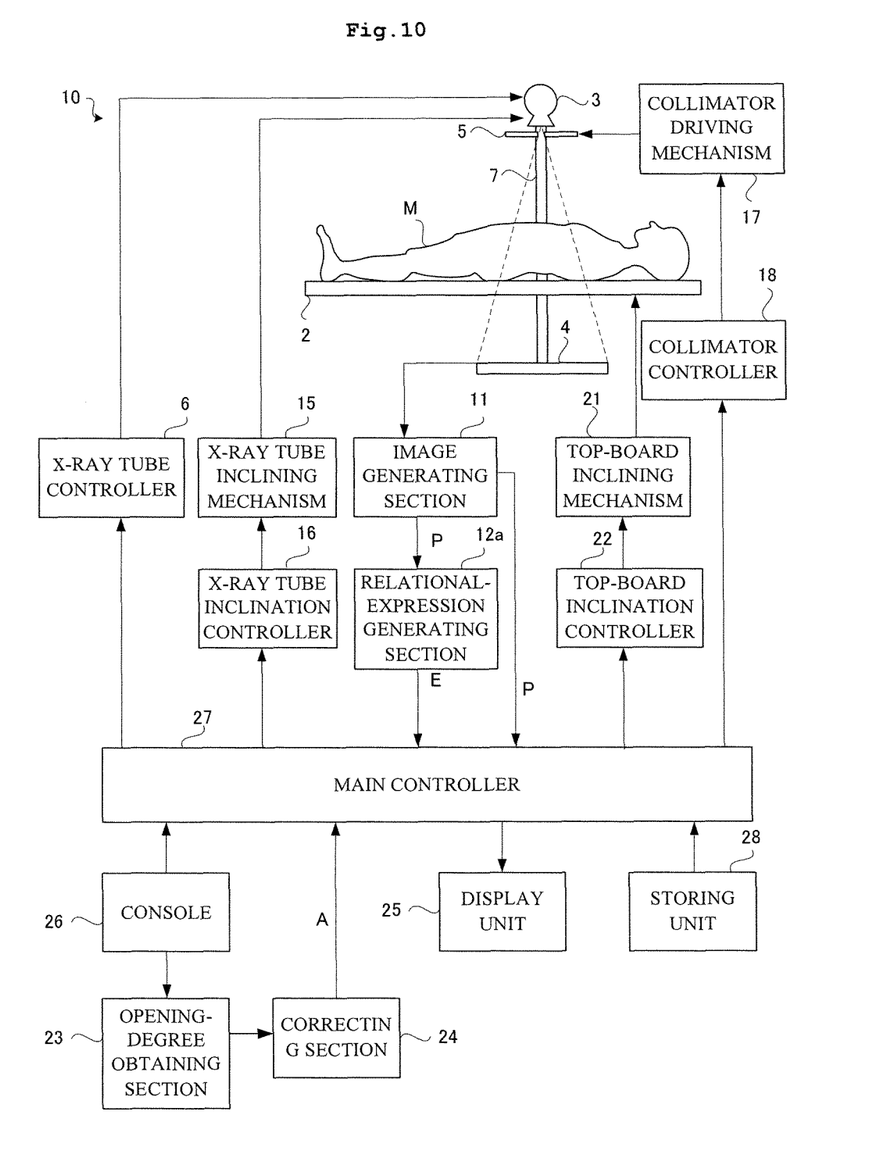
FIG. 10 is a functional block diagram illustrating an X-ray apparatus according to another example.

Description will be given next of an X-ray apparatus 10 according to Example 2. The configuration of the X-ray apparatus 10 in Example 2 is approximately the same as that in Example 1, as shown in FIG. 10. Both differ in that Example 2 has a relational-expression generating section 12a instead of the correlated-table generating section 12, does not have the correlated-table interpolating section 13, and has a correcting section 24 with different operations. These differences are described through explanation of operations of the X-ray apparatus 10 in Example 2.

<Generation of Relational Expression E>

A relational-expression generating section 12a is provided for generating a relational expression E. For generating the relational expression E by the relational-expression generating section 12a, radiography is firstly conducted with the subject not being placed on the top board 2 while a degree of opening of the collimator 5 changes, whereby two or more images P are generated. The obtained images P are sent out to the relational-expression generating section 12a. The relational-expression generating section 12a generates a correlated table T in accordance with a plurality of obtained images P. Here, the correlated table T has a correlation between the degree of opening of the collimator 5 and the width W1 of an X-ray beam (see FIG. 6) contained in the image P.

The relational-expression generating section 12a generates a relational expression E having a relationship between the degree of opening of the collimator 5 and the width W1 of the X-ray beam area in accordance with the correlated table T. Letting the degree of opening of the collimator be x and the width W1 be y, a relational expression is given as under:
$$y = a_1 x^n + a_2 x^{n-1} + \ldots + a_n x + a_{n+1}$$

The relational expression E is an approximate expression indicating a relationship between the degree of opening of the collimator 5 and the width W1 of the X-ray beam area. The storing unit 28 stores coefficients $a_1, a_2, \ldots$ and $a_{n+1}$ in the relational expression generated by the relational-expression generating section 12a.

The collimator 5 has two pairs of leaves 5a, i.e., one pair of leaves 5a that moves along a long-side direction of the top board and one pair of leaves 5a that moves along a short-side direction of the top board. Consequently, two relational expressions E are to be generated individually for each of the two pairs of leaves 5a having different movement directions. The operation is performed in advance prior to radiography of the subject, which is similar to that in Example 1.

<Operation of X-ray Apparatus>

Next, description will be given of operations of the X-ray apparatus 10. In order to image the subject using the X-ray apparatus 10 according to Example 2, a relational expression is firstly generated with the subject not being placed on a top board 2 (corresponding to Step S1 in FIG. 8), and then the subject M is placed on the top board 2 (a placing step S2.) Thereafter, a degree of opening of the collimator 5 is controlled by an operator (an opening-degree variation step S3) to start radiography (a radiography starting step S4.)

As above, the operation of the X-ray apparatus 10 is same as that of the apparatus in Example 1. On the other hand, both differ in operation of the correcting section 24, which is to be described. Example 2 is same as Example 1 in output of the correction value A by the correcting section 24, operation of the collimator controller 18 in accordance with the opening-degree obtaining section, and operation of the display unit 25 in accordance with the correction value A.

<Opening Variation Step S3 in Example 2>

When the operator operates the lever 26b of the slide rheostat 26a on the console 26, an opening-degree obtaining section 23 obtains a degree of opening of the collimator 5 specified through operation by the operator. The degree of opening has a desired value for the degree of opening of the collimator 5 as the operator operates. The collimator controller 18 operates in accordance with the degree of opening of the collimator.

The opening-degree obtaining section 23 sends out the obtained degree of opening of the collimator to the correcting section 24. The correcting section 24 obtains a value of the width of the X-ray beam area (referred to as a correction value A) corresponding to the degree of opening of the collimator in accordance with the coefficients of the relational expression stored in the storing unit 28 and the sent degree of opening of the collimator. Specifically, the correcting section 24 reconstructs the relational expression E using a group of coefficients in the read-out relational expression, and generates the correction value A based on this. The correction value A is sent out to the display unit 25.

The aforementioned configuration in Example 2 shows a specific configuration of the correction data to which the correcting section 24 refers. When the correction data is a relational expression having a relationship between the width of the radiation beam and the degree of opening of the collimator, the same effect as that in the correlated table T can be obtained with a smaller amount of information than the correlated table T. Thereby, the X-ray apparatus has increased flexibility for the elements. That is, the storing unit 28 can be housed in a microcomputer of the X-ray apparatus 1.

This invention is not limited to the foregoing configuration, but may be modified as follows.

(1) The foregoing examples have no description on inclination of the X-ray tube 3. The correlated table T can be generated taking consideration of this. Specifically, the correlated-table generating section 12 generates the correlated table T, and then the X-ray tube 3 is inclined through control of the X-ray tube inclination controller 16. Thereafter, the correlated-table generating section 12 generates again the correlated table T. Such configuration may be adopted. As noted above, inclination of the X-ray tube 3 and generation of the correlated table T is repeated alternately to store the correlated table T for various inclination angles of X-rays and take into consideration inclination of the X-ray tube 3 during operation of the correcting section 24. Thereby an X-ray irradiation area that is displayed on the display unit 25 can be obtained with higher accuracy. The positional relationship of the X-ray tube 3, the collimator 5, and the FPD 4 deviates as the X-ray tube 3 is inclined relative to the FPD 4. Accordingly, the position of the X-ray beam on the detecting surface of the FPD 4 changes as the X-ray tube 3 is inclined. Where the correlated table T generated with the inclination of the X-ray tube 3 conforming to radiography conditions is used upon obtaining the correction value A by the correcting section 24, the X-ray irradiation area is displayed on the display unit 25 taking into consideration influences due to inclination of the X-ray tube 3. Consequently, the operator can recognize an accurate position of X-ray irradiation via the display unit 25 independently of the inclination of the X-ray tube 3.

(2) The foregoing examples have no description on inclination of the top board 2. The correlated table T can be generated taking consideration of this. Specifically, the correlated-table generating section 12 generates the correlated table T, and then the top board 2 is inclined through control of the top-board inclination controller 22. Thereafter, the correlated-table generating section 12 generates again the correlated table T. Such configuration may be adopted. As noted above, inclination of the top board 2 and generation of the correlated table T is repeated alternately to store the correlated table T for various inclination angles of the top board and take into consideration inclination of the top board during operation of the correcting section 24. Thereby an X-ray irradiation area that is displayed on the display unit 25 can be obtained with higher accuracy. Since the X-ray tube 3 is heavy, the strut 7 bends as the top board 2 is inclined. Accordingly, the position of the X-ray beam on the detecting surface of the FPD 4 changes as the top board 2 is inclined. Where the correlated table T generated with the inclination of the top board 2 conforming to radiography conditions is used upon obtaining the correction value A by the correcting section 24, the X-ray irradiation area is displayed on the display unit 25 taking in consideration influences due to inclination of the top board 2. Consequently, the operator can recognize an accurate position of X-ray irradiation via the display unit 25 independently of the inclination of the top board 2.

(3) The foregoing examples have no description on SID (source to image distance). The correlated table T can be generated taking consideration of this. Specifically, the correlated-table generating section 12 generates the correlated table T, and then SID is changed through control top board 2. Thereafter, the correlated-table generating section 12 generates again the correlated table T. Such configuration may be adopted. As noted above, changing SID and generation of the correlated table T is repeated alternately to store the correlated table T for various SID and take into consideration SID during operation of the correcting section 24. Thereby an X-ray irradiation area that is displayed on the display unit 25 can be obtained with higher accuracy. The positional relationship of the top board 2 and the collimator 5 deviates as the top board is moved relative to the X ray tube 3. Accordingly, the position of the X-ray beam on the detecting surface of the FPD 4 changes as the SID is changed. Where the correlated table T generated with the changing SID conforming to radiography conditions is used upon obtaining the correction value A by the correcting section 24, the X-ray irradiation area is displayed on the display unit 25 taking into consideration influences due to SID. Consequently, the operator can recognize an accurate position of X-ray irradiation via the display unit 25 independently of the inclination of the X-ray tube 3.

(4) The modifications concerning the foregoing (1), (2) and (3) are also applicable to Example 2. In this case, the relational expression is generated by the relational-expression generating section 12*a* instead of generating the correlated table T by the correlated-table generating section 12. Moreover, the correcting section 24 refers to a group of coefficients instead of the correlated table T.

(5) The modifications concerning the foregoing (1), (2) and (3) can also be implemented simultaneously. In this case, the correlated table T or the relational expression E is to be prepared corresponding to each combination of an inclination angle of the X-ray tube 3, that of the top board 2 and SID.

The invention claimed is:

1. A radiographic apparatus comprising:
a radiation source for emitting radiation;
a radiation detecting device having a detecting surface for detecting radiation;
a top board for supporting a subject placed thereon between the radiation source and the radiation detecting device;
a radiation-source inclining device for inclining the radiation source relative to the radiation detecting device;
a radiation-source inclination controlling device for controlling the radiation-source inclining device;
an image generating device for generating images in accordance with detection data outputted from the radiation detecting device;
a collimator for restricting spread of a radiation beam emitted from the radiation source;
a console for inputting an operation's instruction;
an opening-degree obtaining device for obtaining a degree of opening of the collimator in accordance with the operator's instruction inputted by the console;
a correcting device for determining a value of a width of the radiation beam corresponding to a current degree of opening using a relationship between widths of the radiation beam contained in the image and degrees of opening, the relationship being obtained in advance through radiation irradiation; and
a display device for displaying a radiation-irradiation area in the radiation detecting device in accordance with the determined value of the width, a relationship between the value of the width and the degree of opening being obtained by inclining while moving the radiation source close to or away from one end of the top board in the longitudinal direction relative to the radiation detecting device to perform radiography for a plurality of times.

2. The radiographic apparatus according to claim 1, wherein
the relationship between the widths of the radiation beam and the degrees of opening of the collimator is a correlated table representing a relationship between the widths of the radiation beam contained in the image obtained through radiation irradiation and the degrees of opening of the collimator.

3. The radiographic apparatus according to claim 2, further comprising:
a correlated-table interpolating device for interpolating the correlated table to generate a new correlated table having an increased number of components than that in the correlated table.

4. The radiographic apparatus according to claim 1, wherein
the relationship between the widths of the radiation beam and the degrees of opening of the collimator is a relational expression having a relationship between the widths of the radiation beam contained in the image obtained through radiation irradiation and the degrees of opening of the collimator.

5. The radiographic apparatus according to claim 1, further comprising:
a top-board inclining device for inclining the top board with a positional relationship between the radiation source and the radiation detecting device being maintained; and
a top-board inclination controller for controlling the top-board inclining device, wherein
the relationship between the widths of the radiation beam and the degrees of opening of the collimator is obtained through conducting radiography two or more times while the top board is inclined.

6. A radiographic apparatus comprising:
a radiation source for emitting radiation;
a radiation detecting device having a detecting surface for detecting radiation;
a top board for supporting a subject placed thereon between the radiation source and the radiation detecting device;
a radiation-source inclining device for inclining the radiation source relative to the radiation detecting device;
a radiation-source inclination controlling device for controlling the radiation-source inclining device;
an image generating device for generating images in accordance with detection data outputted from the radiation detecting device;
a collimator for restricting spread of a radiation beam emitted from the radiation source;
a console for inputting an operation's instruction;
a controller configured to:
obtain a degree of opening of the collimator in accordance with the operator's instruction inputted by the console; and
determine a value of a width of the radiation beam corresponding to a current degree of opening using a relationship between widths of the radiation beam contained in the image and degrees of opening, the relationship being obtained in advance through radiation irradiation; and a display for displaying a radiation-irradiation area in the radiation detecting device in accordance with the determined value of the width, the relationship between the value of the width and the degree of opening being obtained by inclining while moving the radiation source close to or away from one end of the top board in the longitudinal direction relative to the radiation detecting device to perform radiography for a plurality of times.

* * * * *